United States Patent
Fitzmaurice et al.

(10) Patent No.: US 6,368,302 B1
(45) Date of Patent: *Apr. 9, 2002

(54) DILATATION CATHETER WITH STIFFENING WIRE

(75) Inventors: Thomas K. Fitzmaurice, Bushey Park; Patrick J. E. Duane, Newcastle, both of (IE); Denyse Collins, Derry, NH (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/136,330

(22) Filed: Aug. 19, 1998

Related U.S. Application Data

(63) Continuation of application No. 08/387,906, filed as application No. PCT/US93/07943 on Aug. 24, 1993, now Pat. No. 5,823,995, which is a continuation-in-part of application No. 07/934,948, filed on Aug. 25, 1992, now abandoned.

(51) Int. Cl.[7] .............................................. A61M 29/00
(52) U.S. Cl. ........................ 604/103.04; 604/102.01; 604/528; 604/96.01
(58) Field of Search ........................ 604/96–99, 523–5, 604/526, 528, 102.01–102.03, 103, 103.01–103.04, 103.09

(56) References Cited

U.S. PATENT DOCUMENTS

| | | |
|---|---|---|
| 4,351,341 A | 9/1982 | Goldberg et al. |
| 4,546,759 A | 10/1985 | Solar |
| 4,561,439 A | 12/1985 | Bishop et al. |
| 4,614,188 A | 9/1986 | Bazell et al. |
| 4,643,194 A | 2/1987 | Fogarty |
| 4,651,751 A | 3/1987 | Swendson et al. |
| 4,715,378 A | 12/1987 | Pope, Jr. et al. |
| 4,723,936 A | 2/1988 | Buchbinder et al. |
| 4,738,667 A | 4/1988 | Galloway |
| 4,748,982 A | 6/1988 | Horzewski et al. |
| 4,762,129 A | 8/1988 | Bonzel |
| 4,775,371 A * | 10/1988 | Mueller, Jr. .................. 604/98 |
| 4,793,350 A | 12/1988 | Mar et al. |
| 4,819,751 A | 4/1989 | Shimada et al. |
| 4,822,345 A | 4/1989 | Danforth |
| 4,848,344 A | 7/1989 | Sos et al. |
| 4,917,088 A | 4/1990 | Crittenden |
| 4,917,666 A | 4/1990 | Solar et al. |
| 4,932,413 A | 6/1990 | Shockey et al. |
| 4,940,062 A | 7/1990 | Hampton et al. |
| 4,946,466 A | 8/1990 | Pinchuk et al. |
| 4,947,864 A | 8/1990 | Shockey et al. |
| 4,976,689 A | 12/1990 | Buchbinder et al. |
| 4,988,356 A | 1/1991 | Crittenden et al. |
| 4,994,032 A | 2/1991 | Sugiyama et al. |
| 4,998,923 A | 3/1991 | Samson et al. |

(List continued on next page.)

FOREIGN PATENT DOCUMENTS

| | | |
|---|---|---|
| DE | 9207395 | 8/1992 |
| EP | 0344530 | 12/1989 |
| EP | 0 380 873 A2 | 8/1990 |
| EP | 0441384 | 8/1991 |
| WO | 9217236 | 10/1992 |

Primary Examiner—Anhtuan T. Nguyen
Assistant Examiner—Michael M. Thompson

(57) ABSTRACT

A Balloon dilation catheter comprising an elongated tubular shaft and an inner tube defining inflation and guide wire lumens. A dilation balloon is mounted on the distal end of the tubular shaft and communicates with the inflation lumen. The guide wire lumen extends through the balloon. A stiffening wire is positioned within the tubular shaft and has a proximal end secured in the proximal portion of the catheter. The distal end of the stiffening wire is anchored within the inner tube in an area adjacent the guide wire entrance port. The stiffening wire maximizes strength to the proximal portion of the catheter while maintaining flexibility in the distal end of the catheter as well as the balloon.

4 Claims, 3 Drawing Sheets

U.S. PATENT DOCUMENTS

| | | |
|---|---|---|
| 5,002,531 A | 3/1991 | Bonzel |
| 5,002,532 A | 3/1991 | Gaiser et al. |
| 5,035,705 A | 7/1991 | Burns |
| 5,059,176 A | 10/1991 | Winters |
| 5,087,246 A | 2/1992 | Smith |
| 5,090,959 A | 2/1992 | Samson et al. |
| 5,102,403 A | 4/1992 | Alt |
| 5,104,376 A | 4/1992 | Crittenden |
| 5,112,310 A | 5/1992 | Grobe |
| 5,217,482 A | 6/1993 | Keith |
| 5,238,005 A | 8/1993 | Imran |
| 5,242,396 A | 9/1993 | Evard |
| 5,295,961 A | 3/1994 | Neiderhauser et al. |
| 5,328,472 A | 7/1994 | Steinke et al. |
| 5,346,505 A | 9/1994 | Leopold |
| 5,364,357 A * | 11/1994 | Aase .......................... 604/96 |
| 5,380,283 A * | 1/1995 | Johnson ................. 604/103.04 |
| 5,423,754 A | 6/1995 | Cornelius et al. |
| 5,516,336 A | 5/1996 | McInnes et al. |
| 5,531,690 A * | 7/1996 | Solar ..................... 604/103.04 |
| 5,545,134 A | 8/1996 | Hilaire et al. ................. 604/96 |
| 5,567,203 A | 10/1996 | Euteneuer et al. |

* cited by examiner

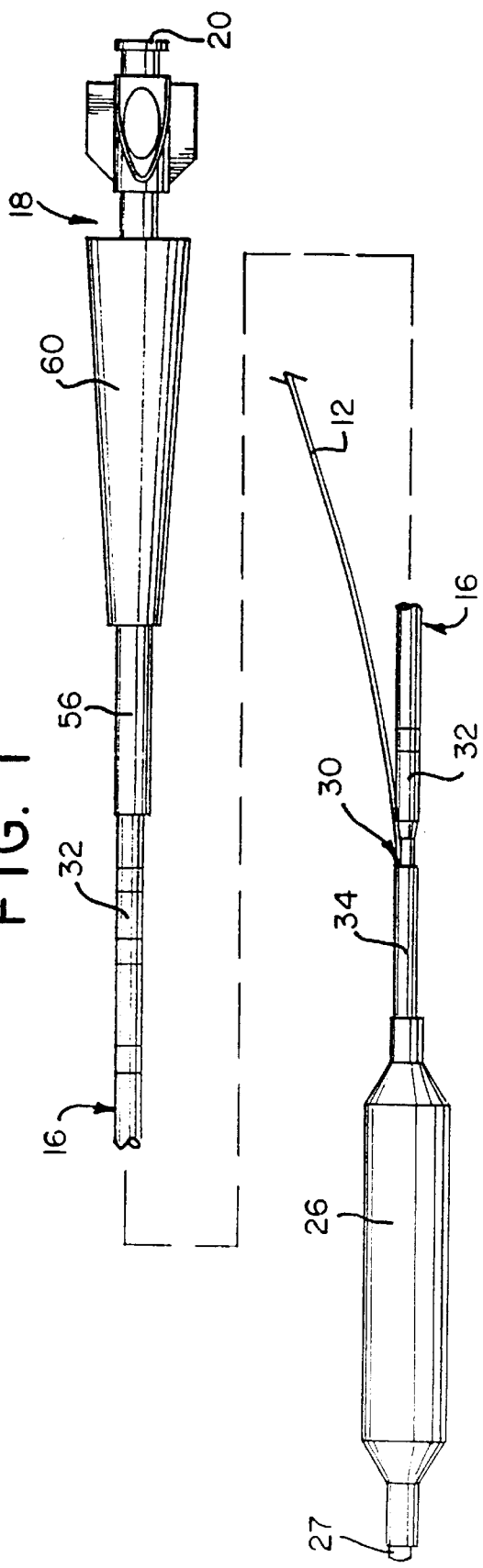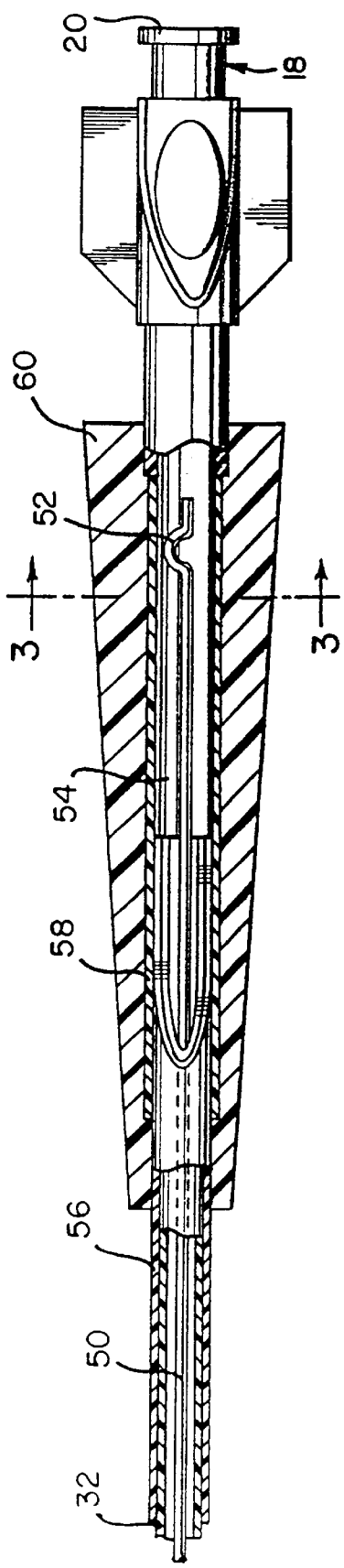
FIG. 1
FIG. 2

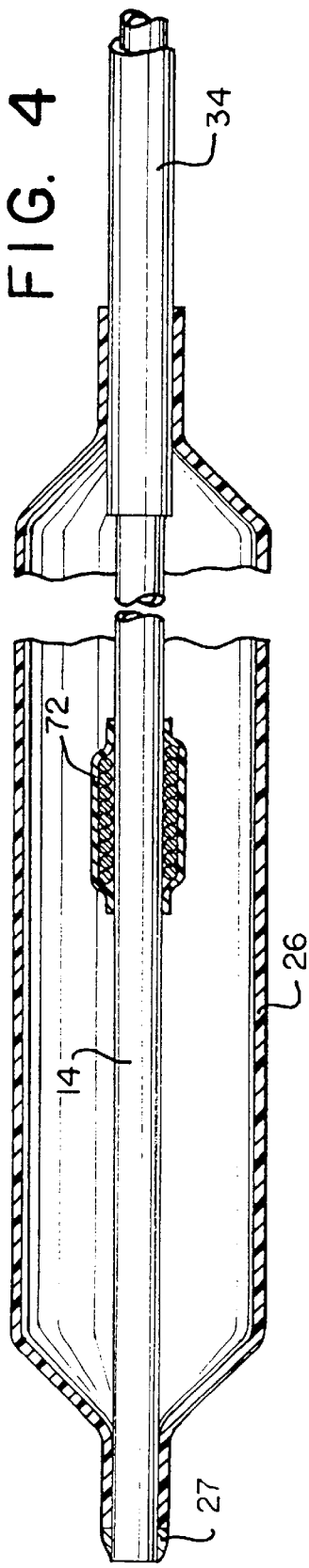
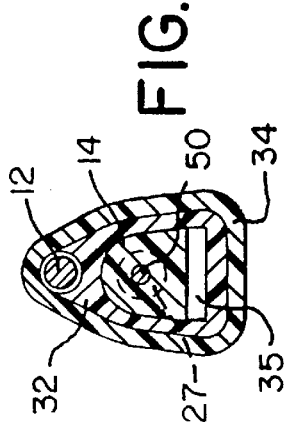
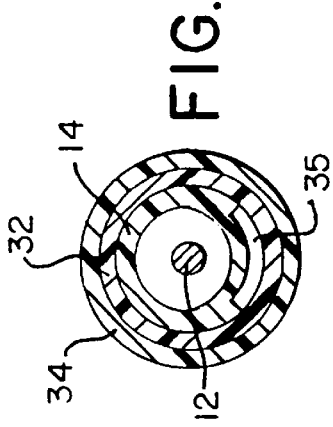
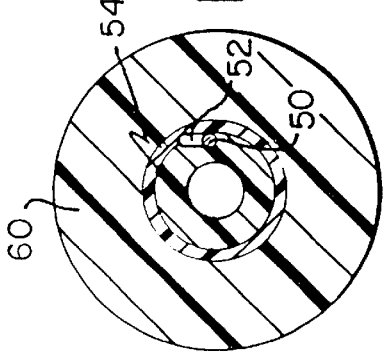
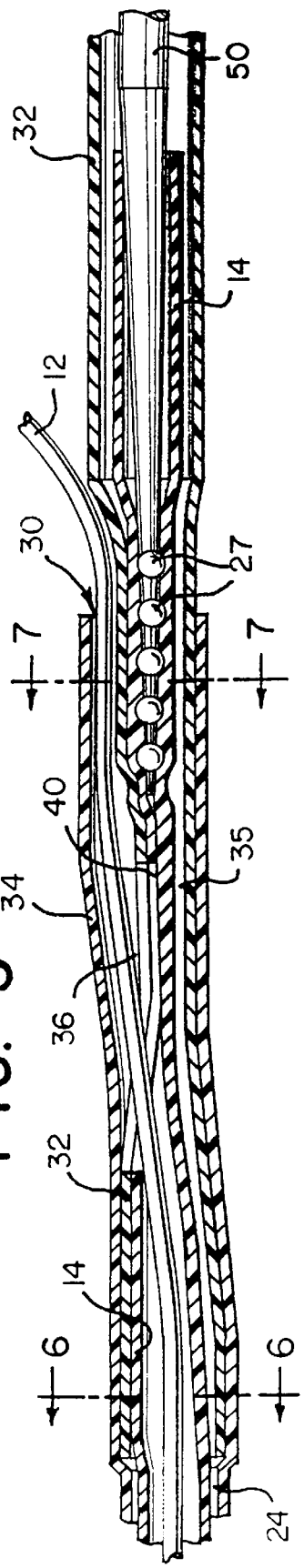

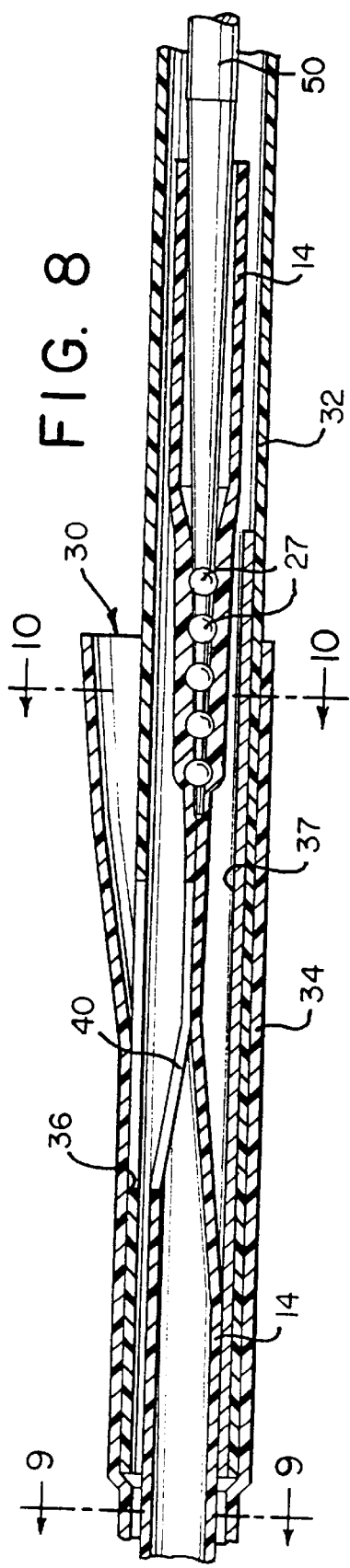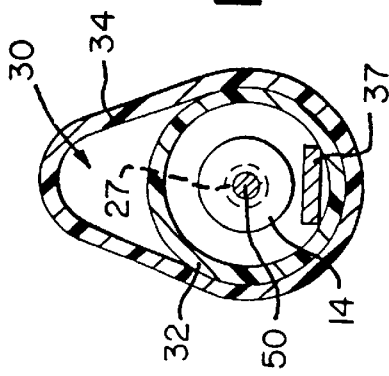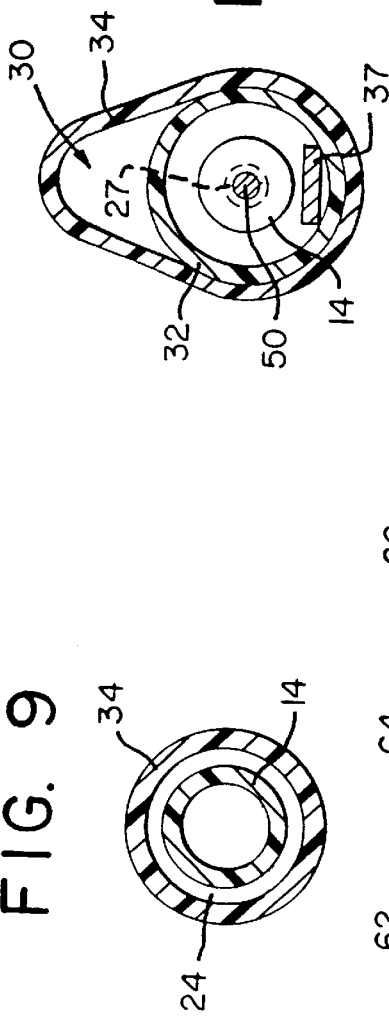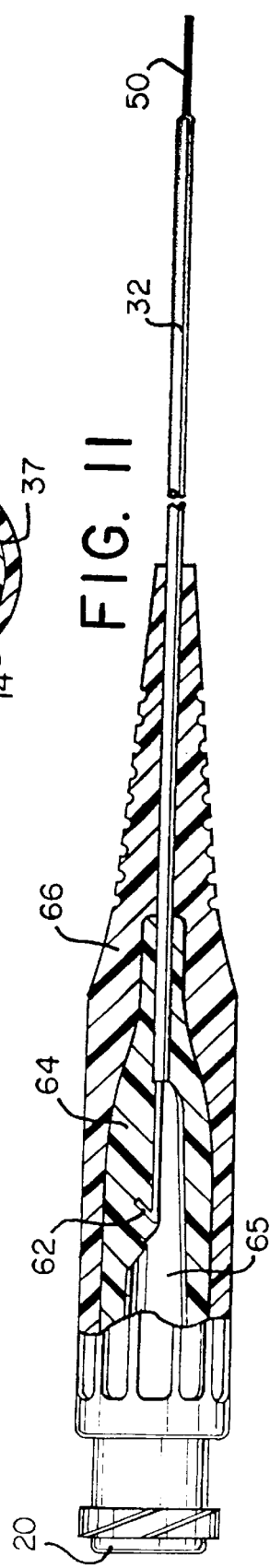

DILATATION CATHETER WITH STIFFENING WIRE

This is a continuation of U.S. patent application Ser. No. 08/387,906, filed Jun. 29, 1995, now U.S. Pat. No. 5,823,995, which is Section 371 of PCT/US93/07943, filed Aug. 24, 1993, which is a continuation-in-part of U.S. patent application Ser. No. 07/934,948 filed Aug. 25, 1992 now abandoned.

FIELD OF THE INVENTION

This invention relates to a dilatation catheter and more particularly to a monorail type dilation catheter having a stiffening wire.

BACKGROUND OF THE INVENTION

Monorail dilatation catheters are commonly used in angioplasty procedures because the unique construction of such catheters enables the rapid exchange of the catheter once it is inserted into the patient. For example, U.S. Pat. No. 4,762,129 to Bonzel discloses a monorail catheter having a short tube defining a guide wire lumen at the distal end of the catheter. The tube extends through the balloon from the distal end to a point proximal of the proximal end of the balloon. This tube terminates at an aperture opening to the exterior of the catheter such that most of the length of the guide wire from the balloon to the proximal end of the catheter is exterior of the catheter. Rapid exchange and manipulation of the dilatation catheter is facilitated because the catheter segment contacting the surface of the guide wire is only as long as the balloon.

Although the monorail catheter provides rapid catheter exchange, it tends to lack stiffness and, therefore, is difficult to push through a patient's blood vessels. In the Bonzel construction, a stiffening wire extends through the catheter imparting stiffness to the catheter. However, the stiffening wire may impart stiffness in areas of the catheter where flexibility is desired, for example in the balloon.

Due to the construction of the catheter, heretofore it has not been feasible to terminate a stiffening wire in a dilatation catheter proximal of the section of the catheter in which flexibility is desired. To provide enhanced flexibility in situations where a stiffening wire is used, tapered stiffening wires have been proposed. Schneider (Europe) AG sells a dilatation balloon catheter in which a tapered stiffening wire "floats" within the catheter, i.e., the stiffening wire is not anchored at its distal and proximal ends. While this construction, in the ideal situation, may provide the requisite stiffness and maintain distal flexibility, the floating stiffening wire is prone to movement which can lead to problems in manipulating the catheter.

OBJECTS OF THE INVENTION

The object of the invention is to provide a dilatation catheter in which a stiffening wire terminates proximal of the distal end of the catheter and is securely anchored in place at both its distal and proximal ends.

A more specific object of the invention is to provide a catheter of the monorail type in which a stiffening wire is anchored at the proximal end of the catheter and wherein the distal end of the stiffening wire terminates at and is secured in place within the catheter in the region of the entrance port for the guide wire.

SUMMARY OF THE INVENTION

In accordance with the present invention, a balloon dilation catheter of the monorail type includes a stiffening wire secured at both its ends in a selected position such that maximum strength is imparted in the proximal portion of the catheter while flexibility is maintained in the distal portion of the catheter and the balloon. In the preferred embodiment, the catheter comprises an elongated tubular shaft with a dilatation balloon mounted on its distal end. An inner tube extends distally from a position proximal of the guide wire port and is adapted to receive the guide wire which is inserted through the port. The space between the tubular shaft and the inner tube provides an inflation lumen for the balloon. In accordance with the invention, a stiffening wire is anchored at its proximal end within the catheter and the distal end of the stiffening wire is retained within the inner tube in the vicinity of the guide wire port.

THE DRAWINGS

FIG. 1 is a schematic plan view of a monorail catheter in accordance with the invention;

FIG. 2 is a plan view partially in section showing one way in which the stiffening wire may be anchored in the luer fitting;

FIG. 3 is a sectional view along the line 3—3 of FIG. 2;

FIG. 4 is a plan view partially in section showing how the dilatation balloon is secured to the distal end of the catheter;

FIG. 5 is a detailed cross-sectional view of a catheter manufactured in accordance with the preferred embodiment of the invention showing the fused laminate in the region of the guide wire port;

FIG. 6 is a sectional view along the line 6—6 of FIG. 5;

FIG. 7 is a sectional view along the line 7—7 of FIG. 5;

FIG. 8 is a detailed sectional view showing the inner tube with the retained stiffening wire inserted into the catheter shaft prior to the final assembly step in which the fused laminate is formed;

FIG. 9 is a sectional view along the line 9—9 of FIG. 8;

FIG. 10 is a sectional view along the line 10—10 of FIG. 8; and

FIG. 11 is a plan view partially in section showing an alternative method for anchoring the proximal end of the stiffening wire within a luer fitting.

DETAILED DESCRIPTION

As shown in FIG. 1, a dilation catheter in accordance with the invention comprises an elongated tubular shaft 16 which consists of a proximal shaft 32 and a distal shaft 34. The distal shaft overlaps the proximal shaft in such a way as to form a guide wire port 30 through which a guide wire 12 can be introduced in conventional fashion. The lumen for the guide wire is formed by an inner tube 14 which may be made of the same material as distal shaft 34, i.e., a flexible heat shrinkable material such as high density polyethylene. Inner tube 14 extends from a point just proximal of the guide wire port 30 to the distal end of the balloon. The proximal end of shaft 32 is connected to a luer fitting 18. A dilatation balloon 26, which may be of convention design, is secured at the distal end of the shaft 34. Fluid introduced through a connector 20 of luer 18 causes balloon 26 to expand in conventional fashion.

In the preferred embodiment, the annular space 24 between the distal shaft 34 and inner tube 14 forms an inflation lumen. The shaft 34 terminates proximal to the distal end of the inner tube 14 (FIG. 4). As shown in FIG. 4, the proximal end of balloon 26 is connected and sealed to the distal end of the distal shaft 34. The inner tube 14 extends through the balloon 26 and is sealed at its distal end to the distal end of the balloon. Adhesive 29 provides a rounded end at the distal end of the balloon.

The balloon 26 is formed from either a noncompliant polyethylene terephthalate (PET) or a more compliant material such as urethane. It is preferred that the balloon is coated with a highly lubricous, abrasion resistant coating. An example of a preferred coating is that disclosed in U.S. Pat. No. 5,077,352 to Elton, and assigned to the assignee of the present invention, C. R. Bard of Murray Hill, N.J., the disclosure of which is incorporated herein by reference. As disclosed in that patent, a flexible, lubricous organic polymeric coating is formed by applying a mixture of an isocyanate, a polyol, poly(ethylene oxide), and a carrier liquid to the surface to be coated. The carrier liquid is removed and the mixture reacted to form a polyurethane coating with associated poly (ethylene oxide) giving a highly lubricous, abrasion resistant, flexible coating.

A radiopaque coil spring 72 is positioned within the balloon 26 around the inner tube 14 (FIG. 4). The coil spring 72 ensures flexibility of the balloon, the distal portion of the catheter, and the tip. The radiopaque coil spring enables the balloon 26 to be identified under X-ray. In one embodiment, the coil was formed from 0.0025 inch spring coil material such as a gold-platinum combination. The formed coil may be about 4.5 mm long. The chosen coil parameters depend on the desired flexibility characteristics to be imparted to the distal end of the catheter.

In accordance with the invention, a stiffening wire 50, tapered at its distal end, extends from the luer 18 axially through proximal shaft 32 to the vicinity of the guide wire port 30 where it is positioned within the inner tube 14. The tapered end of the stiffening wire 50 includes five adhesive beads 27 and is anchored within the proximal end of inner tube 14 by heat shrinking the inner tube to the stiffening wire as explained further below. Slots 40 and 36 are cut in inner tube 14 and proximal shaft 32, respectively, so that the guide wire 12 can be inserted through the port 30 and into the lumen within inner tube 14 distal of port 30. As shown in FIG. 5, the inner tube 14 may be bonded to a distal portion of the proximal shaft 32 and the distal shaft 34 to form a tubular laminate. Since fluid must be introduced into the balloon in the passageway 24 between the inner tube 14 and the distal shaft 34, a fluid passageway 35 is provided from the proximal shaft 32 through the thermally bonded section of the catheter into the region where the distal shaft 34 and inner tube 14 are coaxial. This region starts at the left-hand side of FIG. 5 and extends into the balloon where the distal shaft 34 terminates.

FIG. 2 shows one way in which the proximal end of the stiffening wire 50 may be anchored within the luer fitting 18. The luer fitting 18 includes a cylindrical balloon leg 54, its distal end abutting against the proximal end of the proximal shaft 32. The stiffening wire 50 includes a crimp 52 at its proximal end which passes through the wall of balloon leg 54 so that the crimped portion lies against the exterior surface of the balloon leg 54. Wire 50 is positioned within the balloon leg during the molding process. A strain relief tube 56 envelops the proximal shaft 32 distal of its junction with the balloon leg 54. A shrink tube 58 is placed over the crimped portion of wire 50 and a proximal section of strain relief tube 56 and serves to secure the assembly when heat is applied. The luer may also include a conically shaped cover 60 which is secured to the luer by conventional adhesives and serves partly as a strain relief member.

An alternative structure for anchoring the proximal end of the stiffening wire within the luer fitting is shown in FIG. 11. In this case, the proximal end of the stiffening wire 50 includes a hook 62 which is embedded in a molded insert 64 of the luer during the molding process. The proximal end of the proximal shaft 32 is also embedded within the insert 64 during the molding process. During the molding process, a core pin (not shown) is positioned within the mold to form a lumen 65 to enable the introduction of air into the shaft 32 to inflate the balloon. After the insert 64 is molded, the assembly is over-molded with material 66 to form the finished luer fitting. The over-mold material 66 provides strain relief and is shaped to facilitate manipulation when a source of air is to be connected to the luer.

In the preferred embodiment, the proximal shaft 32 is an extruded polymer tube (for example, high molecular weight high density polyethylene). However, all or part of the proximal shaft 32 may comprise a hypotube in which case the proximal end of the stiffening wire is joined to the distal end of the hypotube rather than to the luer. If the proximal shaft were to consist of a hypotube and extruded polymer tube, the two would be joined together by conventional means.

The precise point at which the stiffening wire so terminates is not critical but it is preferred that the stiffening wire terminate in the vicinity of the guide wire port 30. The point of termination will depend on the desired flexibility of the distal section of the catheter.

Assembly of the preferred embodiment of the catheter according to the invention is as follows. First, the adhesive beads 27 are applied to the distal end of the stiffening wire 50 and cured. Stiffening wire 50 is then inserted into the inner tube 14 with a patency mandrel between the wire and tube in the area where the tube and wire are not to be bonded together. A shrink tube is then placed over the assembly and the inner tube 14 heat welded to the stiffening wire 50. The shrink tube and patency mandrel are removed.

As shown in FIG. 8, the stiffening wire assembly thus formed is then placed in the proximal shaft 32. The proximal end of wire 50 is attached to luer 18 as described above and heat welded into position.

Next, a flat mandrel 37 is positioned between inner tube 14 and proximal shaft 32 to provide for the fluid passageway 35 through the fused laminate after heat welding. Similarly, a patency mandrel (not shown) is positioned in the inner tube 14 to maintain an opening for the guide wire 12. A shrink tube is positioned over this assembly and heat applied to weld the inner tube 14 to proximal shaft 32. The shrink tube and patency mandrel are then removed.

Slots 36 and 40 are then cut through the proximal shaft 32 and inner tube 14 to provide an opening for the guide wire into the lumen within the inner tube 14. A patency mandrel is then placed within the inner tube extending through the slots. The flared distal shaft 32 is inserted over the distal end of the proximal shaft 34 and up over the slots and patency mandrel with the proximal end of the distal shaft 32 overlapping the stiffening wire 50. The shrink tube is applied over the joint area and heat applied to weld the entire assembly to form the fused laminate. The shrink tube is removed and then the patency mandrel and flat mandrel 37 are removed leaving the fused laminate with a guide wire port into the inner tube 14 and the fluid passageway 35 through the fused laminate.

During the welding process, the portion of proximal shaft 32 just proximal of slot 36 is "folded down" into contact with the wire retention section of inner tube 14 to form a sloped wall 38 (FIG. 5). The close positional relation among the guide wire opening 40 of the inner tube 14, the guide wire entrance port 30, and the sloped wall 38 of the proximal shaft 32 forms a smooth transition and passageway for the guide wire into the inner tube 14. The smooth transition and passageway not only aids in initial guide wire placement into the catheter, but also facilitates catheter exchange.

The stiffening wire 50 may be formed from different materials. A 302 or 304 stainless steel has been found satisfactory. Plastics, composite metals, and other materials also can be used as long as the selected material imparts the desired stiffness to the proximal portion of the catheter.

With a catheter that is about 150 cm long, and with a conventional length dilatation balloon, the stiffening wire 50 is about 121 cm long. In one embodiment, the wire is about 0.016 +/–0.0003 inches diameter and tapers down to about a 0.003+/–0.0003 inch diameter cylindrical portion. The tapered portion may be approximately 10+/–0.5 cm long, and the cylindrical portion about 10 mm+/–2 mm. When the wire is formed of a metallic material such as stainless steel, the distal 9 cm may be stress relieved.

The monorail catheter of the present invention offers several benefits over prior art monorail catheters. The use of a stiffening wire anchored proximally at the luer and distally adjacent to the guide wire entrance port enhances pushability, kink resistance at the guide wire entrance port, and the flexibility transition from the proximal portion to the distal portion of the catheter. The use of a single lumen shaft at the proximal portion of the catheter maximizes the inflation/deflation lumen and reduces deflation times to a minimum. The different coaxial inner and outer shaft materials are chosen from materials to enhance performance characteristics. The coaxial distal section minimizes tip distension during balloon inflation.

What is claimed is:

1. A dilatation catheter having a proximal end and a distal end, said catheter comprising:

an elongated tubular shaft comprising a distal shaft having a proximal end and a distal end, a proximal shaft having a proximal end and a distal end, said proximal end of said distal shaft overlapping said distal end of said proximal shaft and a guide wire port for entry of a guide wire into said distal shaft;

a balloon attached to said distal shaft;

an inner tube extending within said tubular shaft from a point proximal of said guide wire port within said proximal shaft through said distal shaft to a point distal of said guide wire port, said inner tube including an opening adjacent said guide wire port to enable a guide wire to be introduced into and extend through said inner tube through said guide wire port and said opening, said inner tube including a wire retention section adjacent said opening, said inner tube being bonded to said tubular shaft, with a space between said inner tube and tubular shaft providing an inflation lumen for said balloon wherein said inner tube, proximal shaft and distal shaft are made of thermoplastic material in the region of said guide wire port, said proximal shaft and inner tube are thermally bonded to said distal shaft to form a fused laminate, said proximal shaft also including an opening adjacent the guide wire port to enable a guide wire to be introduced into said inner tube, and wherein a passageway extends through said fused laminate from said proximal shaft to said inflation lumen; and a stiffening wire positioned within said tubular shaft, said stiffening wire having a distal end permanently anchored in said wire retention section.

2. A dilatation catheter according to claim 1, wherein said wire retention section is thermally bonded to said stiffening wire.

3. A dilatation catheter having a proximal end and a distal end, said dilatation catheter comprising:

an elongated tubular shaft having a guide wire port for entry of a guide wire;

a balloon attached to said tubular shaft;

an inner tube extending within said tubular shaft from a point proximal of said guide wire port to a point distal of said guide wire port, said inner tube including an opening adjacent said guide wire port to enable a guide wire to be introduced into and extend through said inner tube through said guide wire port, said inner tube including a wire retention section adjacent said opening, said inner tube being bonded to said tubular shaft to retain said inner tube relative to said tubular shaft, with a space between said inner tube and tubular shaft providing an inflation lumen for said balloon wherein said inner tube and tubular shaft are made of thermoplastic material and in the region of said guide wire port, said inner tube is thermally bonded to said tubular shaft to form a fused laminate, said tubular shaft also including an opening adjacent the guide wire port to enable a guide wire to be introduced into said inner tube, and wherein a passageway extends through said fused laminate from the interior of said tubular shaft to said inflation lumen; and a stiffening wire positioned within said tubular shaft, said stiffening wire having a distal end permanently anchored to said inner tube in said wire retention section within said inner tube.

4. A dilation catheter having a proximal end and a distal end, said dilation catheter comprising:

an elongated tubular shaft comprising a distal section and a proximal section and having a lumen extending therethrough, said tubular shaft defining a guide wire port between said proximal section and said distal section for entry of a guide wire into said distal section wherein said elongated tubular shaft includes an inner tube which extends from a point proximal of the guide wire port to a point distal of the guide wire port;

a balloon attached to said distal section of said shaft;

a stiffening wire positioned within said lumen of said proximal section and having a distal end permanently anchored within said distal section of said shaft distally of said guide wire port; and a radiopaque coil spring disposed with the balloon and around the inner tube.

* * * * *